US006207110B1

(12) United States Patent
Sullivan et al.

(10) Patent No.: US 6,207,110 B1
(45) Date of Patent: Mar. 27, 2001

(54) METALLIC OVERCOATING AS A LIGHT ATTENUATING LAYER FOR OPTICAL SENSORS

(75) Inventors: Kevin J. Sullivan, Medfield, MA (US); Thomas C. Collins, Linwood, MI (US); Rudolf E. Slovacek, Norfolk, MA (US)

(73) Assignee: Bayer Corporation, E. Walpole, MA (US)

(*) Notice: Subject to any disclaimer, the term of this patent is extended or adjusted under 35 U.S.C. 154(b) by 0 days.

(21) Appl. No.: 09/137,728

(22) Filed: Aug. 21, 1998

(51) Int. Cl.$^7$ .................................................. G01N 21/64
(52) U.S. Cl. ....................... 422/56; 422/82.07; 422/82.08
(58) Field of Search ............................. 422/82.05, 82.06, 422/82.07, 82.08, 82.11, 56, 57

(56) References Cited

U.S. PATENT DOCUMENTS

| 3,992,158 | 11/1976 | Przybylowicz et al. . | |
|---|---|---|---|
| 4,003,707 | 1/1977 | Lübbers et al. . | |
| 4,042,335 | 8/1977 | Clément . | |
| 4,248,829 | 2/1981 | Kitajima et al. | 422/56 |
| 4,255,384 | 3/1981 | Kitajima et al. | 422/57 |
| 4,587,101 | 5/1986 | Marsoner et al. | 422/56 |
| 4,680,268 | 7/1987 | Clark, Jr. | 435/291 |
| 4,752,115 | 6/1988 | Murray, Jr. et al. | 350/96.29 |
| 4,781,890 | 11/1988 | Arai et al. | 422/56 |
| 4,810,655 | 3/1989 | Khalil et al. | 436/138 |
| 4,857,472 | 8/1989 | Wolfbeis | 436/122 |
| 4,895,156 | 1/1990 | Schulze | 128/634 |
| 4,895,704 | 1/1990 | Arai et al. | 422/57 |
| 4,919,891 | 4/1990 | Yafuso et al. | 422/58 |
| 5,026,139 | * 6/1991 | Klainer et al. | 350/96.29 |

(List continued on next page.)

FOREIGN PATENT DOCUMENTS

| 0409033 | 7/1990 | (EP) . |
| 0442276 | 1/1991 | (EP) . |
| 0584721 | 8/1993 | (EP) . |
| 87/00023 | 1/1987 | (WO) . |
| 90/07107 | 6/1990 | (WO) . |
| 95/30148 | 11/1995 | (WO) . |
| 97/37210 | 10/1997 | (WO) . |

OTHER PUBLICATIONS

MacCraith et al., "Optical Chemical Sensors Based on Sol–Gel Materials: Recent Advances and Critical Issues", *J. Sol–Gel Sci. and Tech.*, vol. 8, pp. 1053–1061 (1997).

Papkovsky et al., "Phosphorescent Polymer Films for Optical Oxygen Sensors", *Biosensors & Electronics* 7, pp 199–206 (1991).

Roffey, "Photopolymerization of Surface Coatings", *Wiley–Interscience*, p. 110–117 (1985).

Salame, M. "Transport Properties of Nitrile Polymers", *J. Polymer Sci. Symp.* 41, pp 1–15 (1973).

*Primary Examiner*—Jeffrey Snay
(74) *Attorney, Agent, or Firm*—Reed & Associates

(57) ABSTRACT

A liquid permeable metallic coating is utilized in conjunction with a fluorescence based optical sensor. The metallic coating is deposited directly on, and is in physical contact with, the sensing membrane. The metallic coating does not require an intervening substrate layer or other components. When light from a light source is shone through the substantially light transmissive substrate onto the sensing membrane, the metallic overcoating reflects back the excitation light as well as the fluorescence light generated by the sensor such that substantially no light reaches the sample where the light may be scattered and/or absorbed by the sample. Accordingly, the accuracy and repeatability of the sensor is improved while the cost and production times associated with manufacturing the sensor are minimized.

10 Claims, 4 Drawing Sheets

U.S. PATENT DOCUMENTS

| | | | |
|---|---|---|---|
| 5,030,420 | 7/1991 | Bacon et al. | 422/82.07 |
| 5,043,286 | 8/1991 | Khalil et al. | 436/136 |
| 5,075,127 | 12/1991 | Yafuso et al. | 427/2 |
| 5,081,041 | 1/1992 | Yafuso et al. | 436/68 |
| 5,081,042 | 1/1992 | Yafuso et al. | 436/68 |
| 5,091,800 | 2/1992 | Offenbacher et al. | 359/350 |
| 5,173,432 | 12/1992 | Lefkowitz et al. | 436/138 |
| 5,208,147 | 5/1993 | Kagenow et al. | 435/14 |
| 5,326,531 | 7/1994 | Hahn et al. | 422/82.06 |
| 5,341,805 | 8/1994 | Stavridi et al. | 128/633 |
| 5,462,879 | 10/1995 | Bentsen | 436/136 |
| 5,609,823 | 3/1997 | Harttig et al. | 422/66 |
| 5,629,213 * | 5/1997 | Kornguth et al. | 436/518 |
| 5,631,340 | 5/1997 | Olstein | 528/59 |
| 5,866,433 * | 2/1999 | Schalkhammer et al. | 426/525 |

\* cited by examiner

METALLIC OVERCOATING AS A LIGHT ATTENUATING LAYER FOR OPTICAL SENSORS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Fluorescent based optical sensors wherein a sensing membrane is layered onto a light transmissive substrate are known. The sensing membrane of the sensor is brought into contact with a sample while an excitation light reaches the sensing membrane through the substrate. The combination of the excitation light, the sensing membrane and a particular analyte will cause the sensing membrane to emit a fluorescing light. The emission signal from the sensing membrane is then detected through the light transmissive substrate from the back side of the sensor. Due to the fact that the sensing membranes of the sensor are quite thin there is a fairly large amount of the excitation light which passes through the sensing membrane and into the sample or into the sample chamber. The light which passes through the sensing membrane may be scattered, absorbed or reflected by the sample or the chamber walls back into and through the sensing membrane. Additionally, the fluorescing signal emitted from the sensing layer, which is indicative of the detection of the amount of the analyte of interest of the sample under test, may also be absorbed, scattered or reflectedly the sample back to the detector. The scattering, absorbing or reflecting of the excitation light and the fluorescing light emitted by the sensing membrane can combine to provide a four fold change in the signal between a perfectly reflecting and perfectly absorbing signal, thus severely skewing the detection results of the sensor.

Previous attempts to address this issue of unintended light affecting the results of the sensor include coating the sensing membrane with a support layer material which has been impregnated with a second material, or coating the sensing membrane with a plurality of layers such that the amount of light escaping the sensor into the sample and sample chamber is a very small fraction of the total light directed to the sensor. These attempts utilized a complex chemical process to produce an opaque, chemically permeable multilayered structure which is then laminated onto the sensing membrane. For example, U.S. Pat. No. 5,091,800 discloses the construction of an ion permeable cover membrane formed from a cross linked PVOH or cellophane substrate which is stretched onto a form and impregnated with silver, gold or platinum colloidal precipitants through a series of chemical treatments to form the opaque membrane. U.S. Pat. Nos. 5,081,041 and 5,081,042 disclose the use of an ion permeable cover membrane fabricated from a Dextran or cellulose substrate and impregnated with detergent solvated carbon black. U.S. Pat. Nos. 4,919,891 and 5,075,127 utilize cellulose acetate/acetone mixtures of either copper pthalocyanine or carbon black cast as separate coating membranes. U.S. Pat. No. 3,992,158 discloses the incorporation of a separate $TiO_2$-containing cellulose acetate for opacity or reflectance to be used in absorbance based chemistries on dry slides. Similarly, U.S. Pat. Nos. 4,042,335, 4,781,890, 4,895,704 and EP 0 142 849 B1 disclose the use of light blocking layers incorporating $TiO_2$ particles for slide based chemistry tests. Such techniques have proven to be complex, labor intensive and expensive, requiring the utilization of multiple components or multiple layers of materials. It would be desirable to provide an inexpensive and simple to produce sensor including a single light attenuating layer of material deposited directly on the sensing membrane which reflects excitation and emission light back into the sensor without the light being affected by the sample while permitting the analyte of interest to freely diffuse through the light attenuating layer and into the sensing membrane.

BRIEF SUMMARY OF THE INVENTION

A liquid permeable metallic coating is utilized in conjunction with a fluorescence based optical sensor. The metallic coating is deposited directly on, and is in physical contact with, the sensing membrane. The metallic coating does not require an intervening support layer of material, or other components. When light from a light source is shone through the substantially light transmissive substrate onto the sensing membrane, the metallic overcoating reflects back the excitation light as well as the fluorescence light generated by the sensor such that substantially no light reaches the sample where the light may be scattered and/or absorbed by the sample. Reflectance from within the sample cavity is also avoided. Accordingly, the accuracy and repeatability of the sensor is improved while the cost and production times associated with manufacturing the sensor are minimized.

BRIEF DESCRIPTION OF THE SEVERAL VIEWS OF THE DRAWING

The invention will be more fully understood from the following detailed description taken in conjunction with the accompanying drawings in which.

DETAILED DESCRIPTION OF THE INVENTION

Figure 1:
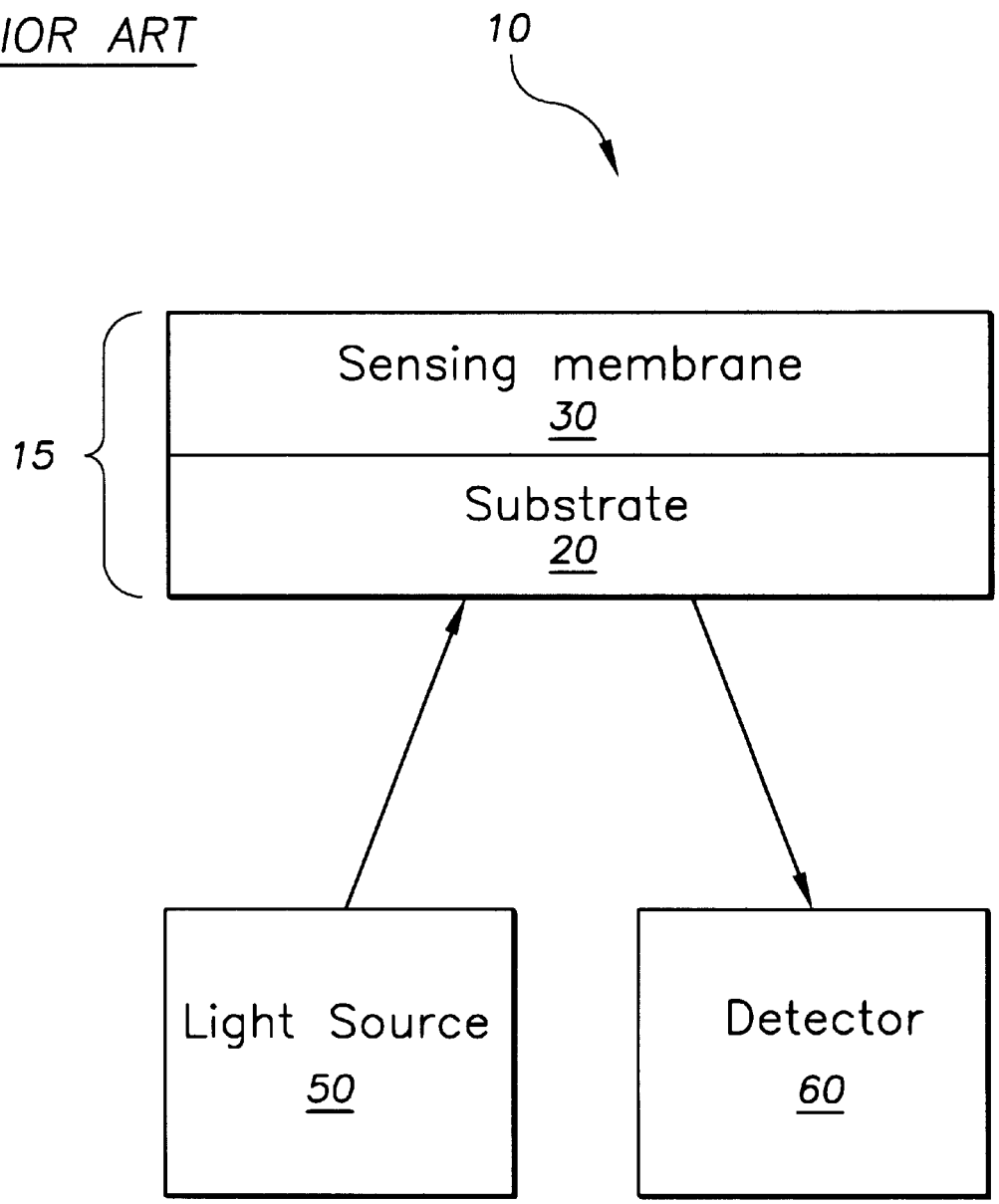
FIG. 1 is a block diagram of a prior art sensor.

A prior art sensing system 10 is shown in FIG. 1 and includes a sensor 15, a light source 50, and a detector 60. Sensor 15 comprises a light transmissive substrate 20 having a sensing membrane 30 layered thereon. In operation, sensing membrane 30 is brought into contact with a sample (not shown) being tested. The light source 50 provides an excitation light to substrate 20, such as through an optical fiber. Substrate 20 is generally light transmissive, thus the light from light source 50 passes through substrate 20 and falls on sensing membrane 30. Sensing membrane 30, in the presence of the excitation light and in the presence of a particular analyte in the sample will emit a fluorescing light to a degree defined by the concentration of the analyte in the sample. This fluorescing light provided by sensing membrane 30 will pass through substrate 20 and be detected by the detector 60.

Since sensing membrane 30 is relatively thin, excitation light also passes through the membrane 30 and into the sample. Once the excitation light is received by the sample it may be scattered, absorbed and/or reflected back through the sensing membrane 30, and through substrate 20 to be detected by detector 60. Additionally, the fluorescing light produced by the sensing membrane may also pass through sensing membrane 30 and into the sample where it may be scattered, absorbed and/or reflected. Again, this light may pass through sensing membrane 30 and through substrate 20 where it will be detected by detector 60. Accordingly, the measurement results of the sensor can be skewed greatly.

Figure 2:
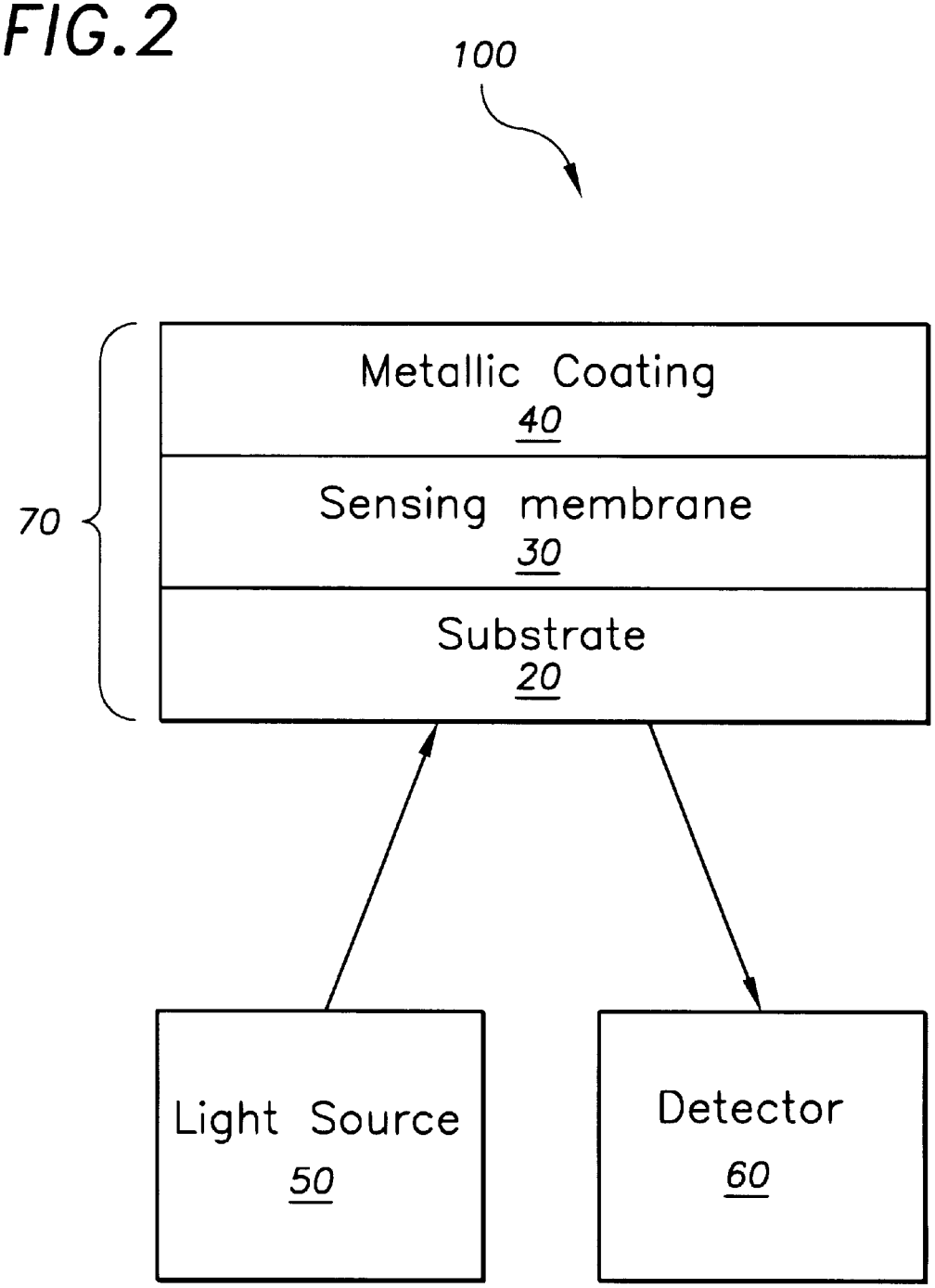
FIG. 2 is a block diagram of a sensor including the metallic coating of the present invention.

Referring to FIG. 2 a sensing system 100 is shown. The system 100 includes a sensor 70, a light source 50 and a detector 60. The light source 50 and detector 60 are in communication with the sensor 70 through any suitable means, including a fiber optic channel. Sensor 70 includes a substrate 20, a sensing membrane 30 layered on the substrate 20 and a metallic coating 40 layered on the sensing membrane 30. Substrate 20 may be made of any substantially light transmissive material such as cellulose acetate, cellulose acetate butyrate, polyethylene terephthalate, bisphenol A polycarbonate, polystyrene, polymethyl methacrylate or preferably glass.

The sensing membrane 30 is deposited onto a surface of the substrate 20. The sensing membrane 30 may comprise any material or group of materials formed together which provide a detectable indication in response to exposure to a specific analyte of the sample. In a preferred embodiment the sensing membrane 30 is made of copolymer JB3001/23 which comprises a mixture of ethylhexylmethacrylate, methylmethacrylate and an oxygen sensing dye such as octa-ethyl-Pt-porphyrin (OEP).

The sensor 70 further includes a liquid permeable metallic overcoating 40 which is generally nontransmissive to light. The metallic overcoating 40 may comprise Aluminum, $TiO_2$ or preferably a Gold Palladium mixture. The metallic overcoating 40 may be deposited onto the sensing membrane 30 by sputter coating, evaporating or other means, thus no intervening support layer or substrate is required between the metallic coating 40 and the sensing membrane 30.

The metallic coating may have an optical density of between approximately 0.2 and approximately 0.893.

In operation, metallic coating 40 is brought into contact with a sample (not shown) being tested. Metallic coating 40 is liquid permeable such that the sample can diffuse through metallic coating 40 and contact sensing membrane 30. The light source 50 provides an excitation light to substrate 20. Substrate 20 is generally light transmissive, thus the light from light source 50 passes through substrate 20 and falls on sensing membrane 30. Sensing membrane 30 in the presence of the excitation light and in the presence of a particular analyte of the sample will emit a fluorescing light. This fluorescing light provided by sensing membrane 30 will pass through substrate 20 and be detected by a detector 60.

Since sensing membrane 30 is relatively thin, light also passes through the membrane 30 and onto metallic coating 40. Metallic coating 40 is generally nontransmissive to light and reflects the light back through the sensing membrane 30 without allowing a significant amount of the light to reach the sample where the light can be affected by the sample and be subsequently detected by detector 60. Additionally, the fluorescing light produced by the sensing membrane may also pass through sensing membrane 30 where it will also encounter metallic coating 40. Once again, metallic coating 40 will reflect the light back to the sensor without a significant amount of the light passing through to the sample where the light may be affected by the sample and subsequently detected by the detector 60. Accordingly, the excitation light and fluorescing light are not affected by the sample, thus the sensor provides a much more accurate and repeatable sensing of analytes.

Figure 3A:
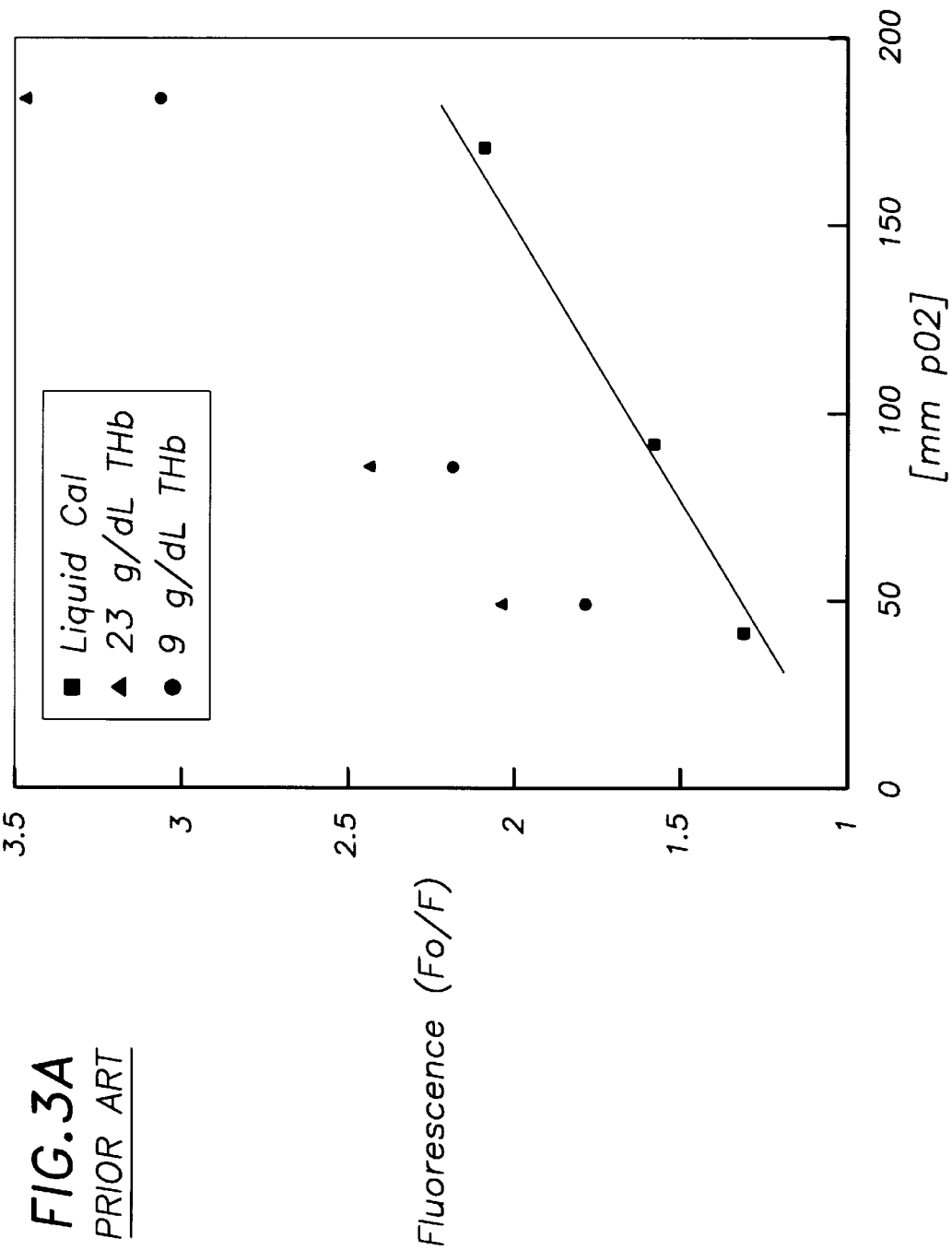
FIG. 3A is a graph of test results for the prior art sensor of FIG. 1.

Referring now to FIG. 3A a Stern/Volmer plot of a fluorescence intensity in response to varying levels of oxygen is shown as detected by a prior art sensor. A clear, aqueous buffer solution was plotted (denoted by the squares) as was a sample having twenty three grams per deciliter of total hemoglobin (THb) (denoted by triangles) and a sample having nine grams per deciliter of THb (denoted by circles). As seen from the plot, the samples having different THb levels produced a large difference in fluorescence, which can be attributed to the presence and detection of interfering light, such as excitation light which has been scattered, absorbed and reflected by the sample as well as fluorescing light which has been reflected, absorbed or scattered by the sample and has been detected by the detector.

Figure 3B:
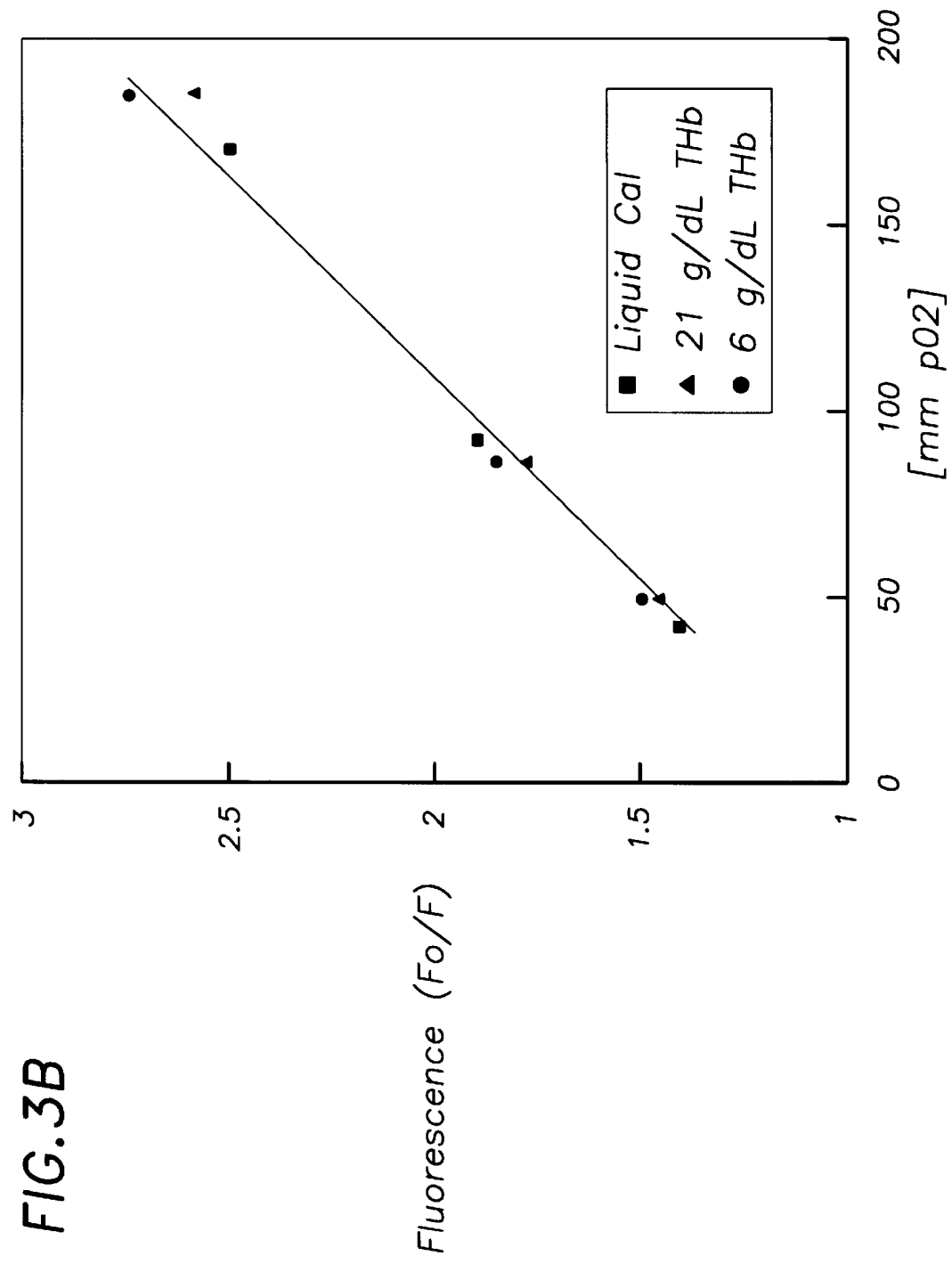
FIG. 3B is a graph of test results for the sensor including the metallic coating of the present invention.

Referring now to FIG. 3B it can be seen that the same tests performed using similar solutions with the sensor of the present invention provide a much more uniform response. The sensor here has a liquid permeable metallic coating which has an optical density of approximately 0.893. A Stern/Volmer plot of a fluorescence intensity in response to varying levels of oxygen is shown as detected by the sensor of the present invention. A clear, aqueous buffer solution was plotted (denoted by the squares) as was a sample having twenty one grams per deciliter of THb (denoted by triangles) and a sample having six grams per deciliter of THb (denoted by circles). As seen from the plot, the samples having different THb levels produced a generally uniform fluorescence, which can be attributed to the absence of interfering light, such as excitation light which has been scattered, absorbed and reflected by the sample as well as fluorescing light which has been reflected, absorbed or scattered by the sample. Due to the inclusion of the metallic coating directly on the sensing membrane, very little light passes through the metallic coating and to the sample where in can be reflected, absorbed or scattered and provide interfering light which skews the results.

The incorporation of a metallic coating which is liquid permeable as well as being generally nontransmissive to light provides a substantial improvement in the repeatability of sample testing and for testing a variety of different samples. The metallic coating is applied directly onto the sensing membrane without the use of an intervening support layer or without the use of multiple layers of materials thus providing a cost effective manner of including the metallic overcoating since additional materials and labor are minimized, while performance and reliability are greatly improved.

Having described preferred embodiments of the invention it will now become apparent to those of ordinary skill in the art that other embodiments incorporating these concepts may be used. Accordingly, it is submitted that the invention should not be limited to the described embodiments but rather should be limited only by the spirit and scope of the appended claims.

We claim:

1. A sensor comprising:
   a substrate substantially transmissive to light having a first side and a second side;
   a sensing membrane layered onto the second side of said substrate; and
   a liquid permeable, substantially nontransmissive to light metallic coating comprising gold and palladium directly layered on said sensing membrane.

2. The sensor of claim 1 wherein said metallic coating is sputter coated onto said sensing membrane.

3. The sensor of claim 1 wherein said metallic coating is evaporated onto said sensing membrane.

4. The sensor of claim 1 wherein said metallic coating has an optical density of between approximately 0.2 and approximately 0.893.

5. The sensor of claim 1 wherein said sensing membrane comprises a mixture of ethylhexylmethacrylate, methylmethacrylate and an oxygen sensing dye.

6. The sensor of claim 5 wherein said oxygen sensing dye comprises octa-ethyl-Pt-porphyrin (OEP).

7. The sensor of claim 1 wherein said substrate comprises glass.

8. The sensor of claim 1 wherein said substrate is selected from the group consisting of cellulose acetate, cellulose acetate butyrate, polyethylene terephthalate, bisphenol A polycarbonate, polystyrene, and polymethyl methacrylate.

9. The sensor of claim 1 further comprising:
- a light source in communication with said substrate, said sensing membrane and said metallic coating; and
- a detector in communication with said substrate, said sensing membrane and said metallic coating.

10. A sensor comprising:
- a substrate substantially transmissive to light having a first side and a second side;
- a sensing membrane layered onto the second side of said substrate; and
- a liquid permeable, substantially nontransmissive to light metallic coating comprising gold and palladium layered directly on said sensing membrane, said metallic coating having an optical density of approximately 0.893;
- a light source in communication with said substrate, said sensing membrane, and said metallic coating; and
- a detector in communication with said substrate, said sensing membrane and said metallic coating.

* * * * *